United States Patent
Kozak, III

[11] Patent Number: 6,054,060
[45] Date of Patent: Apr. 25, 2000

[54] LIQUID PURFICATION SYSTEM AND METHOD FOR DECONTAMINATING MICROBE INFESTED LIQUID

[75] Inventor: Andrew F. Kozak, III, Media, Pa.

[73] Assignee: Aquitic Technology Inc., Media, Pa.

[21] Appl. No.: 09/196,345

[22] Filed: Nov. 19, 1998

[51] Int. Cl.[7] .................................................. C02F 1/02
[52] U.S. Cl. ...................... 210/774; 210/187; 210/256; 422/38; 422/307; 165/DIG. 162
[58] Field of Search .................... 210/774, 177, 210/187, 252, 256, 162; 165/132, 165, DIG. 513; 422/38, 307

[56] References Cited

U.S. PATENT DOCUMENTS

| | | |
|---|---|---|
| 110,638 | 1/1871 | Eaton . |
| 783,880 | 2/1905 | Malcom . |
| 839,926 | 1/1907 | Griffith . |
| 1,297,171 | 3/1919 | Holley et al. . |
| 1,678,819 | 7/1928 | Koch . |
| 2,009,510 | 7/1935 | Mobley . |
| 2,182,428 | 12/1939 | Fladmark . |
| 2,307,078 | 1/1943 | Reed . |
| 2,353,382 | 7/1944 | Barrett . |
| 3,151,677 | 10/1964 | Thompson et al. . |
| 3,296,122 | 1/1967 | Karassik et al. . |
| 3,647,624 | 3/1972 | Evenson . |
| 3,856,492 | 12/1974 | Klass . |
| 3,925,149 | 12/1975 | Erwin . |
| 4,452,671 | 6/1984 | Oakes . |
| 5,294,351 | 3/1994 | Clum et al. . |
| 5,315,921 | 5/1994 | Davis . |
| 5,552,057 | 9/1996 | Hughes et al. . |
| 5,891,330 | 4/1999 | Morris . |

Primary Examiner—David A. Simmons
Assistant Examiner—Fred Prince
Attorney, Agent, or Firm—Rosenberg, Klein & Lee

[57] ABSTRACT

A liquid purification system (10) and method for decontaminating microbe infested liquid (14) is provided. The liquid purification system (10) includes a primary tank (18) which contains both a purifying liquid composition (24) and an initially treated microbe infested liquid (44) with the liquids being immiscible with respect to each other. A heating element (30) is immersed in the primary tank (18) for heating the purifying liquid composition (24). Microbe infested liquid (14) passes through a secondary conduit (16) and is inserted into the primary tank (18) where the microbe infested liquid (14) is heated by contact with the heat purifying liquid composition (24) and descends to a lower portion of the primary tank (18). A primary conduit (34) is mounted within the primary tank (18) and secondarily heats the initially treated microbe infested liquid (44) to provide a purified liquid composition.

22 Claims, 1 Drawing Sheet

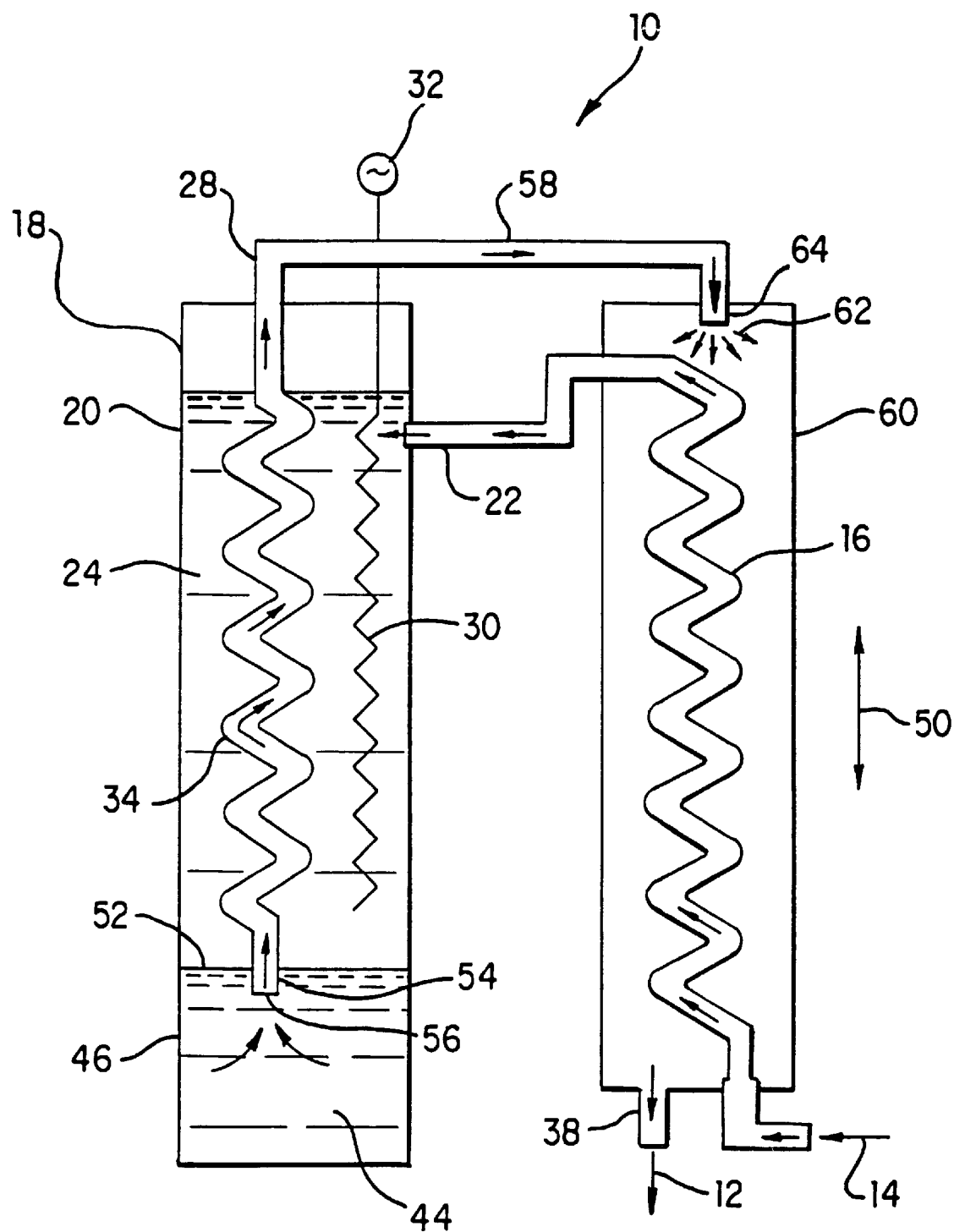

LIQUID PURIFICATION SYSTEM AND METHOD FOR DECONTAMINATING MICROBE INFESTED LIQUID

BACKGROUND OF THE INVENTION

1. Field of the Invention

This invention directs itself to liquid purification systems and methods for decontaminating microbe infested liquids. In particular, this invention relates to a microbe decontamination structure which provides a high efficiency system for destroying microbes in a liquid. Still further, this invention directs itself to a liquid purification system where two immiscible liquids are used for chemical reaction isolation and liquid-to-liquid thermal transfer between the liquids in a manner whereby microbes are destroyed. Still further, this invention relates to a liquid purification system where a microbe infested liquid is passed through a heated purifying liquid composition by gravity assist and the temperature of the microbe infested liquid is raised to a point which destroys the microbes contained therein. Additionally, this invention relates to a liquid purification system where microbe infested liquid is passed by gravity assist through an electrically heated immiscible fluid composition to provide an efficient liquid-to-liquid transfer of heat. Further, this invention relates to a system where initially treated liquid, after passing through an immiscible purifying liquid composition is returned to the heated portion of the purifying liquid composition for further heating of the initially treated liquid to produce a substantially purified liquid. More in particular, this invention directs itself to a system whereby the substantially purified liquid is further placed in heat exchange relation with incoming micro-infested liquids for pre-heating the microbe-infested liquids prior to its insertion into a tank containing the heated purifying liquid composition.

2. Prior Art

Liquid purification systems and methods therefor are known in the art. The best prior art known to Applicant includes U.S. Pat. Nos. 3,647,624; 783,880; 1,678,819; 2,307,078; 110,638; 2,353,382; 3,296,122; 3,925,149; 2,182,428; 3,856,492; 1,297,171; 2,009,510; and, 5,552,057.

U.S. Pat. No. 3,647,624 is directed to a treatment of blood with an oleaginous substance such as vegetable oil. In this type of system, a vessel is partially filled with a synthetic or natural oil. Blood is then introduced through an open end at the top of the vessel and by the differences in specific gravity and immiscibility between the blood and oil, the blood passes continuously through the body of oily material and collects to form a layer at the bottom of the vessel. However, this system is not directed to the combined element concept of passing microbe infested liquid through a heated immiscible fluid composition, as is necessary to the subject invention concept with the further heating of an initially treated liquid and heat exchange necessary to provide an efficient purification system as described with respect to the subject system.

U.S. Pat. No. 783,880 is directed to a system for heating and purifying oil. Apparently, oil is maintained in a tank and rotated and water is introduced at a top end which sinks through the oil by reason of its higher specific gravity. In some manner, impurities contained within the water pass to the bottom of the tank, however, once again, this does not provide for the combined elements for the purposes and objectives of the subject liquid purification system including the heating of the liquid purifying system and then a re-heating process of the treated liquid as is necessary to the subject invention system.

U.S. Pat. No. 1,678,819 is directed to a process for removing hydrochloric acid from sugar solutions. A stream of hot oil is supplied to a tank through an inlet pipe and concurrently the solution to be freed of hydrochloric acid is supplied under pressure to a spray nozzle. The spray of solution containing the hydrochloric acid falls from the spraying device onto the hot surface of the oil and the hydrochloric acid is vaporized. Once again, this reference does not provide for the combined elements of the subject liquid purification system including both heat exchange and re-heating of the treated liquid, as well as pre-heating of any microbe infested liquid with the contiguous interface of the immiscible compositions, as is provided by the subject Patent Application system and method.

U.S. Pat. No. 839,926 is directed to a method of destroying organisms in water and other liquids. Contaminated liquid is introduced into a purifying chamber wherein it is heated. The treated liquid exits the treatment chamber and is introduced into a preheating chamber where it pre-heats infested liquid prior to its introduction into the purifying chamber. This reference fails to teach the concept, let alone details for the combined elements of the subject system, including, for example, further heating of an initially heated and treated liquid, within the purifying chamber, which improves the overall efficiency of the purification system of the present invention over prior art systems.

SUMMARY OF THE INVENTION

This invention provides a liquid purification system and method for decontaminating microbe infested liquid. A mechanism is provided for containing a purifying liquid composition and the microbe infested liquid in a purifying chamber of a tank. The purifying liquid composition and the microbe infested liquid must be immiscible each with respect to the other. An electrical heating mechanism heats the purifying liquid composition and the microbe infested liquid is passed through the heat purifying liquid composition whereby the microbe infested liquid is heated by contact with the heated purifying liquid composition for destroying microbes contained in the microbe infested liquid resulting in a purified liquid.

BRIEF DESCRIPTION OF THE DRAWINGS

The FIGURE is a schematic drawing of the liquid purification system for decontaminating microbe infested liquids showing both the incoming microbe infested liquid and the treated output liquid free of microbes.

DESCRIPTION OF THE PREFERRED EMBODIMENTS

Referring now to the FIGURE, there is shown liquid purification system 10 and a method for decontaminating microbe infested liquid being inserted within water supply line 14. The main purpose and objective of liquid purification system 10 is to treat water or other liquid from incoming water supply 14 and deliver a treated output water or other treated liquid which has been decontaminated with respect to microbes contained in the incoming water supply 14.

Although applicable to all microbe infested liquid supplies, the subject system 10 has specific application to water containing cryptosporidium. Cryptosporidium is predominant in animal fecal matter and has been found specifically toxic to persons who are afflicted with the AIDS virus. However, the overall concept as provided in following paragraphs is applicable to bacteria laden liquid and particularly to bacteria laden water. The overall concept in decontamination or destruction of microbes contained within incoming water supply 14 is through a gradual heating process which efficiently maintains the temperature of the water being treated to a sufficiently high temperature for a predetermined time which will effectively kill or destroy the microbes within the liquid. In particular, the subject system 10 is provided to efficiently allow heating over an extended period of time which will result in the destruction of the microbes. For the specific case of cryptosporidium, it has been found that if the liquid containing cryptosporidium is maintained at a temperature of 160° F. for fifteen seconds or longer, the cryptosporidium is effectively destroyed.

In overall concept, system 10 operates on a principle of liquid-to-liquid heat exchange where microbe infested liquid 14 passes through a purifying liquid absorbing heat and raising the temperature in a transient manner throughout a predetermined time interval to allow the microbe infested liquid 14 to raise its temperature above that which would destroy a particular microbe. Of importance is that the interface between the purifying liquid composition and the microbe infested liquid 14 be immiscible each with respect to the other, as will be detailed in following paragraphs.

Referring now to the FIGURE, untreated water or other liquid 14 is inserted into system 10 through secondary conduit 16 at ambient temperatures generally approximately in the range of 40°–70° F. The incoming microbe infested liquid 14 passes upwardly through secondary conduit 16 and is inserted into container or primary tank 18 at a top section 20 thereof. Primary tank 18 includes tank inlet 22 for insert of microbe infested liquid 14 being carried in secondary conduit 16. Primary tank or container 18 includes purifying liquid composition 24 in combination with microbe infested liquid 14 being inserted therein. Primary tank 18 thus defines purifying chamber 26 within which purifying liquid composition 24 and microbe infested liquid 14 reside. Purifying liquid composition 24 and microbe infested liquid 14 are immiscible each with respect to the other for purposes and objectives as will be described in following paragraphs. Primary tank or container 18 includes liquid inlet 22 and liquid or primary tank outlet 28 both located at an upper portion or section of tank 18. Primary tank 18 extends in a vertical direction as defined by directional arrow 50 to allow flow of microbe infested liquid 14 through purifying liquid composition 24 by gravity assist.

Purifying liquid composition 24 may be a hydrocarbon liquid or other liquid which has the property of being immiscible with respect to the microbe infested liquid 14. In specific, olive oil has been used as the purifying liquid composition 24, however, any hydrocarbon based liquid composition may be utilized wherein the specific gravity of the particular purifying liquid composition 24 is less than the specific gravity of the incoming microbe infested liquid 14. This allows passage of liquid 14, which generally has a specific gravity approximating 1.0, through composition 24 by gravity assist.

Purifying liquid composition 24 is heated by electrical means such as an electric heating element 30 operated from some power supply 32 external to system 10. Heating element 30 may be any one of a number of commercially available electrical heating elements not important to the inventive concept as herein described, with the exception that it have sufficient heating capability to heat purifying liquid composition 24 to a range approximating 200° F.–250° F. Alternative forms of heating elements 30 may be used such as electrical probe members or heating coils.

As can be seen in the FIGURE, as microbe infested liquid 14 enters tank 18, it contiguously contacts purifying liquid composition 24 and due to the immiscibility of the contacting liquids, no liquid composition interaction occurs. The microbe infested liquid 14 is displaced through purifying liquid composition 24 by gravity assist and since purifying liquid composition 24 has a lower specific gravity than microbe infested liquid 14, the purifying liquid composition 24 is raised to the upper section of tank 18. Additionally, as microbe infested liquid 14 passes downwardly and through purifying liquid composition 24, there is a direct liquid-to-liquid heat exchange process which efficiently raises the temperature of microbe infested liquid 14 to a desired level which can be up to and above 185° F. In this manner, the microbe infested liquid is initially heated and treated within primary tank member 18.

After passing down through purifying liquid 14, the treated micro-infested liquid passes through meniscus 52, defining a planar interface between purifying liquid 14 and the initially treated micro-infested liquid 44 therebelow, and collects within lower section 46 of purifying chamber 26. Coiled primary conduit 34 within primary tank 18 has lower end 54 thereof extending into the lower section 46 of primary tank 18, and particularly, into the volume of initially treated microbe-infested liquid 44 collected below meniscus 52. Primary conduit 34 extends upwardly from its lower end 54 through heated purifying liquid composition 24 and is coupled at an upper end thereof to tank outlet 28. Initially treated microbe-infested liquid 44 below meniscus 52 is driven by fluidic pressure through primary conduit inlet 56 and into re-heating primary conduit 34 wherein it flows upwardly against gravitational forces toward and then through tank outlet 28, as shown in the FIGURE. As the initially treated microbe-infested liquid traverses primary conduit 34, it is secondarily heated (or re-heated) by thermal exchange between primary conduit 34 and heated purifying liquid composition 24, so that a substantially purified liquid is expelled or discharged from primary tank 18 through tank outlet 28 within the approximate temperature range of between 195° F. and 212° F., depending on the temperature of the heated purifying liquid composition 24 and the temperature of the incoming microbe infested liquid 14 introduced into tank 18 through tank inlet 22.

The fluidic pressure within the volume of initially treated microbe infested liquid 44 below meniscus 52 that drives the expulsion of liquid 44 from primary tank 18 against gravity is generated responsive to the following factors and conditions. First, the weight of the liquid in primary tank 18 bearing down upon the volume of initially treated microbe infested liquid 44 below meniscus 52 creates pressure therein. Second, primary tank 18 presents essentially a closed system having fluid inlet 22 and fluid outlet 56 (the inlet into primary conduit 34). When this closed system is at capacity, that is, when the tank is full, due to the incompressibility of purifying liquid composition 24, any additional fluid entering the system at inlet 22 must be accompanied by the expulsion of a corresponding amount of liquid from the tank, through the path of least resistance, namely, up through primary conduit 34. Under these conditions, essentially, the initially treated microbe infested liquid is expelled from primary tank 18 through outlet 28, as substantially purified liquid, at the rate at which microbe infested liquid enters the tank through conduit 22. Since the inflow and outflow (or discharge) rates are substantially equivalent, the level or height of meniscus 52 in primary tank 18 remains correspondingly constant so that the lower end and inlet of primary conduit 34 remain at all times below the meniscus. Overall, so long as fluid is being injected into the primary tank 18, the aforementioned process is, by virtue of the fluidic pressure developed within the tank lower section, self-perpetuating.

The substantially purified liquid expelled from primary tank 18 through tank outlet 28 traverses feedback conduit 58 in the direction shown by the arrows in the FIGURE, to be introduced into an upper section or top end of vertical counterflow heat exchange chamber or secondary tank 60. The substantially purified liquid 62 introduced into counterflow heat exchange chamber 60 at the upper section thereof, through outlet 64 provided at an end of feedback conduit 58, cascades downwardly within chamber 60 and into thermal contact with an outer surface of coiled secondary conduit 16 extending upwardly within counterflow heat exchange chamber 60, and carrying within incoming microbe infested liquid 14. In this manner, the substantially purified liquid 62 and secondary conduit 16 serve as a thermal transfer mechanism whereby the initially introduced microbe infested liquid 14 is preheated as it is carried toward tank inlet 22.

The now treated liquid, introduced into the top end of chamber 60, exits from chamber 60 at system outlet 38 thereof to provide a treated water supply 12 which is substantially free of microbes.

The substantially purified liquid 62 can be introduced into the upper section of chamber 60 in the liquid state, as steam, or as a combination of the two, depending on the temperature at which it is expelled from tank 18 through tank outlet 28. If the heated purifying liquid composition 24 is maintained at a sufficiently high temperature so that the substantially purified liquid expelled from tank 18 reaches a temperature of 212° F., then steam is introduced into the upper section of chamber 60. When such is the case, the steam condenses on the outer surface of secondary conduit 16, thus providing distilled water at system outlet 38.

By way of example, a prototype liquid purification system has been constructed wherein both the primary and secondary tanks have vertical heights and diameters approximating 6 feet and 6 inches, respectively. Using ¼ inch conduits and 3,000 watts of heating power, the prototype system produces substantially purified liquid at a rate of 1 liter per minute purified liquid, having an output temperature approximating 200° F. when the temperature of the input liquid is 60° F. Prototype system temperature measurements indicate that a liquid (initially treated liquid and substantially purified liquid) temperature is maintained throughout the entire system at a minimum level of 180° F., thus destroying microbes carried therein.

Additionally, liquid purifying system 10 as has hereinbefore been described provides a method of decontaminating microbe infested liquid 14 from an incoming water supply. The steps of decontaminating the microbe infested liquid 14 includes the step of providing a purifying liquid composition 24 maintained in primary tank member 18 within purifying chamber 26. The purifying liquid composition is generally a hydrocarbon composition which is immiscible with respect to the microbe infested liquid 14 and has a specific gravity less than the incoming microbe infested liquid 14.

The purifying liquid composition 24 is then heated by way of heating element 30 which simply may be a coil or electric probe type of heating member.

The microbe infested liquid 14 is passed through the heated purifying liquid composition 24 by gravity assist for transferring heat from the heat purifying liquid composition 24 to the microbe infested liquid 14 for destroying microbes and producing a heated, initially treated liquid, which is established at a lower section of purifying chamber 26 of primary tank 18.

Due to the immiscibility of the purifying liquid composition 24 and the microbe infested liquid 14, there is no chemical reaction between the two liquids with the exception of heat transfer in a liquid-to-liquid contiguous interfacing manner.

The method of decontaminating the microbe infested liquid 14 includes the step of pre-heating the microbe infested liquid 14 prior to the passage of the liquid 14 through the heat purifying liquid composition 24 through a heat exchange process within secondary tank member 60 comprised of heat transport between secondary conduit 16 and substantially purified liquid 62 introduced into an upper section of the secondary tank, as is shown in the FIGURE.

The method of decontamination further includes the step of further heating initially treated microbe infested liquid 44 subsequent to passing the microbe infested liquid 14 through the heated purifying liquid composition 24 (which produced the treated microbe infested liquid), but prior to its removal or discharge from primary tank 18. This method is accomplished by passing initially treated microbe infested liquid 44 through conduit inlet 56 into primary conduit 34 wherein it is then driven upwardly by fluidic pressure through the heated purifying liquid composition 24 for thermal exchange purposes and further increasing the temperature of initially treated microbe infested liquid 44 for use in the heat exchange process with the incoming microbe infested liquid 14, as previously discussed.

In the subject liquid purification system 10 and the method for decontaminating the microbe infested liquid 14, it is of importance that the purifying liquid composition 24 and the microbe infested liquid 14 be immiscible each with respect to the other. In this manner, there can be contiguous interface between the liquid while maintaining a chemical reaction isolation. Additionally, of necessity, it is clear that the purifying liquid composition 24 must have a specific gravity less than the specific gravity of the microbe infested liquid 14 to allow passage therethrough by gravity assist of the microbe infested liquid 14. In this manner, the microbes contained within liquid 14 are destroyed as they reach elevated temperature in their passage through purifying liquid composition 24.

Although this invention has been described in connection with specific forms and embodiment thereof, it will be appreciated that various modifications other than those discussed above may be resorted to without departing from the spirit or scope of the invention. For example, functionally equivalent element may be substituted for those specifically shown and described, proportional quantities of the elements shown and described may be varied, and in the formation method steps described, particular steps may be reversed or interposed, all without departing from the spirit or scope of the invention as defined in the appended Claims.

What is claimed is:

1. A liquid purification system for decontaminating microbe infested liquid, comprising:

(a) primary tank means for containing a purifying liquid composition and an initially treated microbe infested liquid, said purifying liquid composition and said microbe infested liquid being immiscible each with respect to the other, said purifying liquid composition being located in an upper section of said primary tank means and said initially treated microbe infested liquid being located in a lower section of said primary tank means;

(b) means for heating said purifying liquid composition;

(c) means for passing said microbe infested liquid through said heated purifying liquid composition for initially heating said microbe infested liquid whereby said microbe infested liquid is heated by contact with said heated purifying liquid composition for destroying microbes contained in said microbe infested liquid to produce said initially treated microbe infested liquid; and, (d) primary conduit means located within said primary tank means in thermal contact with said heated purifying liquid for secondarily heating said initially treated microbe infested liquid to provide a substantially purified liquid.

2. The liquid purifying system as recited in claim 1 where said primary tank means includes a primary tank member having a liquid inlet and a liquid outlet, said microbe infested liquid being inserted into said tank member through said liquid inlet and said substantially purified liquid being removed from said tank through said liquid outlet.

3. The liquid purification system as recited in claim 2 where said primary tank member extends in a vertical direction, said liquid inlet being in fluid communication with said primary tank member upper section and said liquid outlet being in fluid communication with said primary tank member lower section and discharging said substantially purified liquid from said upper section of said primary tank member.

4. The liquid purification system as recited in claim 2 where said means for passing includes first conduit means in fluid communication with said upper section of said primary tank member for insertion of said microbe infested liquid therein.

5. The liquid purification system as recited in claim 4 where said purifying liquid composition has a specific gravity less than said microbe infested liquid.

6. The liquid purification system as recited in claim 5 where said microbe infested liquid passes through and in thermal contact with said purifying liquid by gravity assist.

7. The liquid purification system as recited in claim 1 where said purifying liquid composition is a liquid hydrocarbon composition.

8. The liquid purification system as recited in claim 7 where said liquid hydrocarbon composition is olive oil.

9. The liquid purification system as recited in claim 1 where said means for heating includes electric heating means.

10. The liquid purification system as recited in claim 9 where said purifying liquid composition is heated to a temperature within the approximate range of 200° F. to 250° F.

11. The liquid purification system as recited in claim 9 where said substantially purified liquid is heated to a temperature within the approximate range of 160° F. to 212° F. subsequent to said initial and secondary heating within said primary tank member.

12. The liquid purification system as recited in claim 1 including means for preheating said microbe infested liquid prior to insertion into said upper section of said primary tank means.

13. The liquid purification system as recited in claim 12 where said means for preheating includes counterflow heat exchange means for transferring heat from said substantially purified liquid to said microbe infested liquid.

14. The liquid purification system as recited in claim 13 where said counterflow heat exchange means includes a vertically directed secondary tank means defining a secondary tank member including secondary conduit means for transferring said microbe infested liquid upwardly through said secondary tank member and inlet means for introducing said substantially purified liquid into an upper section of said secondary tank member and into contact with an outer surface of said secondary conduit means.

15. The liquid purification system as recited in claim 1 where said primary conduit means extends through said upper section of said primary tank means and includes an inlet located below a meniscus formed by said purifying liquid composition and said initially treated microbe infested liquid.

16. The liquid purification system as recited in claim 3 where said primary conduit means includes a coiled conduit extending between said liquid outlet and said primary tank member lower section for transferring said initially treated microbe infested liquid therebetween.

17. The liquid purification system as recited in claim 16 where said initially treated microbe infested liquid is passed through said primary conduit means against the force of gravity by fluidic pressure developed within said primary tank member.

18. A method of decontaminating microbe infested liquid comprising the steps of:

(a) providing a purifying liquid composition in a primary tank member, said purifying liquid composition being immiscible with respect to said microbe infested liquid;

(b) heating said purifying liquid composition;

(c) passing said microbe infested liquid through said heated purifying liquid composition for transferring heat from said heated purifying liquid composition to said microbe infested liquid for destroying microbes to produce an initially treated microbe infested liquid; and, (d) further heating said initially treated microbe infested liquid within said tank member subsequent to said passing step to produce a substantially purified liquid.

19. The method as recited in claim 18 where the step of passing said microbe infested liquid includes the step of displacing said microbe infested liquid by gravity assist through said purified liquid composition.

20. The method as recited in claim 18 further including the step of pre-heating said microbe infested liquid prior to insertion into said primary tank member.

21. The method as recited in claim 18 further including the step of expelling said substantially purified liquid from said primary tank member against the force of gravity by fluidic pressure developed within said primary tank member.

22. The method as recited in claim 21 where the steps of further heating and expelling are performed substantially contemporaneously.

* * * * *